United States Patent
Zhou et al.

(10) Patent No.: US 10,590,377 B2
(45) Date of Patent: Mar. 17, 2020

(54) MICROBIAL EXPERIMENT COOLING AND TEMPERATURE-SENSING MULTIPURPOSE RACK

(71) Applicant: HEBEI UNIVERSITY OF SCIENCE AND TECHNOLOGY, Shijiazhuang (CN)

(72) Inventors: Xiaohui Zhou, Shijiazhuang (CN); Le Xu, Shijiazhuang (CN); Jun Liu, Shijiazhuang (CN); Hao Liu, Shijiazhuang (CN)

(73) Assignee: HEBEI UNIVERSITY OF SCIENCE AND TECHNOLOGY, Shijiazhuang (CN)

( * ) Notice: Subject to any disclaimer, the term of this patent is extended or adjusted under 35 U.S.C. 154(b) by 0 days.

(21) Appl. No.: 15/882,996

(22) Filed: Jan. 29, 2018

(65) Prior Publication Data

US 2018/0155670 A1  Jun. 7, 2018

Related U.S. Application Data

(60) Division of application No. 14/831,854, filed on Aug. 20, 2015, now Pat. No. 9,914,904, which is a continuation of application No. PCT/CN2014/082652, filed on Jul. 21, 2014.

(30) Foreign Application Priority Data

Jul. 25, 2013  (CN) .................... 2013 2 0448092 U

(51) Int. Cl.
*C12M 1/34*   (2006.01)
*B01L 9/06*   (2006.01)

(52) U.S. Cl.
CPC ............... *C12M 41/12* (2013.01); *B01L 9/06* (2013.01)

(58) Field of Classification Search
CPC ..................................................... C12M 41/12
USPC ...................................................... 435/307.1
See application file for complete search history.

(56) References Cited

U.S. PATENT DOCUMENTS

2007/0286775 A1* 12/2007 Yong .................... B01L 3/0293
                                                              422/400
2014/0171829 A1*  6/2014 Holmes ............ A61B 5/150305
                                                              600/575

* cited by examiner

*Primary Examiner* — Kevin Joyner
*Assistant Examiner* — Holly Kipouros
(74) *Attorney, Agent, or Firm* — Schwegman Lundberg & Woessner, P.A.

(57) ABSTRACT

A multi-function cooling and thermo-sensitive rack includes horizontal bars, a base, positioning holes, connectors, a lateral frame, connecting holes, a temperature-displaying prompter, and N temperature sensors. The lateral frame and the base are connected through the connectors. The lateral frame and the base have their surfaces facing each other symmetrically provided with plural connecting holes thereon. The horizontal bars have two ends thereof received in the corresponding symmetrical connecting holes. The positioning holes are distributed over the surface of the base. The N temperature sensors have output ends thereof for outputting sensing signals connected with input ends of the temperature-displaying prompter for inputting the N temperature-sensing signals. The present invention is applied to apparatuses used in microbiology experiment.

12 Claims, 6 Drawing Sheets

MICROBIAL EXPERIMENT COOLING AND TEMPERATURE-SENSING MULTIPURPOSE RACK

CROSS REFERENCE TO RELATED APPLICATIONS

This application is a divisional of Ser. No. 14/831,854 filed Aug. 20, 2015, which is a continuation of PCT/CN2014/082652 filed 2014 Jul. 21, which claims priority to CN 201320448092.0 filed 2013 Jul. 25, all of which are incorporated herein by reference.

TECHNICAL FIELD

The present invention relates to apparatuses used in microbiology experiments.

DESCRIPTION OF RELATED ART

Currently, inoculation loops and applicators prepared for sterile experiment on a clean bench are placed directly on the bench surface and are later sterilized by open flame from an alcohol burner before use. After such dry heat sterilization, the sterilized tools have to be held in operators' hands until they become cool, and this causes great inconvenience during the experiment. Particularly, for experiment where different bacteria have to be incubated or different plates have to be prepared, the loops and/or applicators need open-flame sterilization after each time of use, and this is quite time-consuming. Moreover, the temperatures of the processed inoculation loops and/or applicators and of culture medium in Erlenmeyer flasks that has been sterilized are measured only relying on operators' experience. Once such empirical determination is faulty, the result of the experiment can be adversely affected, in turn highly risking the efficiency of the experiment.

SUMMARY OF THE INVENTION

One objective of the present invention is to provide a multi-function cooling and thermo-sensitive rack for microbiology experiment that eliminates the problems in the prior art that during experiment the operators have to hold inoculation loops and/or applicators sterilized by open flame from an alcohol burner in hands for cooling and that the merely empirically determined temperature of culture medium sterilized by steam might be inaccurate and in turn adversely affects the accuracy of the experimental results.

The disclosed multi-function cooling and thermo-sensitive rack for microbiology experiment comprises horizontal bars each having a plurality of semicircular positioning dents, a base, connectors, a lateral frame, connecting holes, a temperature-displaying prompter, and N temperature sensors, where N is an integer greater than or equal to one, wherein the lateral frame is a U-shaped frame, the base is U-shaped, the base has positioning holes, the lateral frame and the base are dimensionally identical to each other, the lateral frame and the base are connected through the connectors, the arms of the U-shaped frame of the lateral frame are provided symmetrically with plural connecting holes, wherein the horizontal bars are horizontally fixed to and mounted over the connecting holes, and wherein the N temperature sensors are arranged at N temperature-measured sites, respectively, and the N temperature sensors have output ends for outputting temperature-sensing signals connected with the input ends of the temperature-displaying prompter for inputting N temperature-sensing signals.

The present invention features the heat resistant horizontal bars that are arranged on the lateral frame having a plurality of positioning dents and the base having a plurality of positioning circular holes, and also features the angular adjustability between the base and the lateral frame, so that inoculation loops and/or applicators can be placed between the positioning dents on the lateral frame and the positioning circular holes of the base. The disclosed rack is structurally simple and angularly adjustable and can be assembled according to its use. With the temperature sensors that measure temperatures in a real-time manner and with the temperature-displaying control unit that displays the measured temperatures, experiment can be significantly improved in terms of accuracy and efficiency.

DETAILED DESCRIPTION OF THE INVENTION

Embodiment 1

Figure 1:
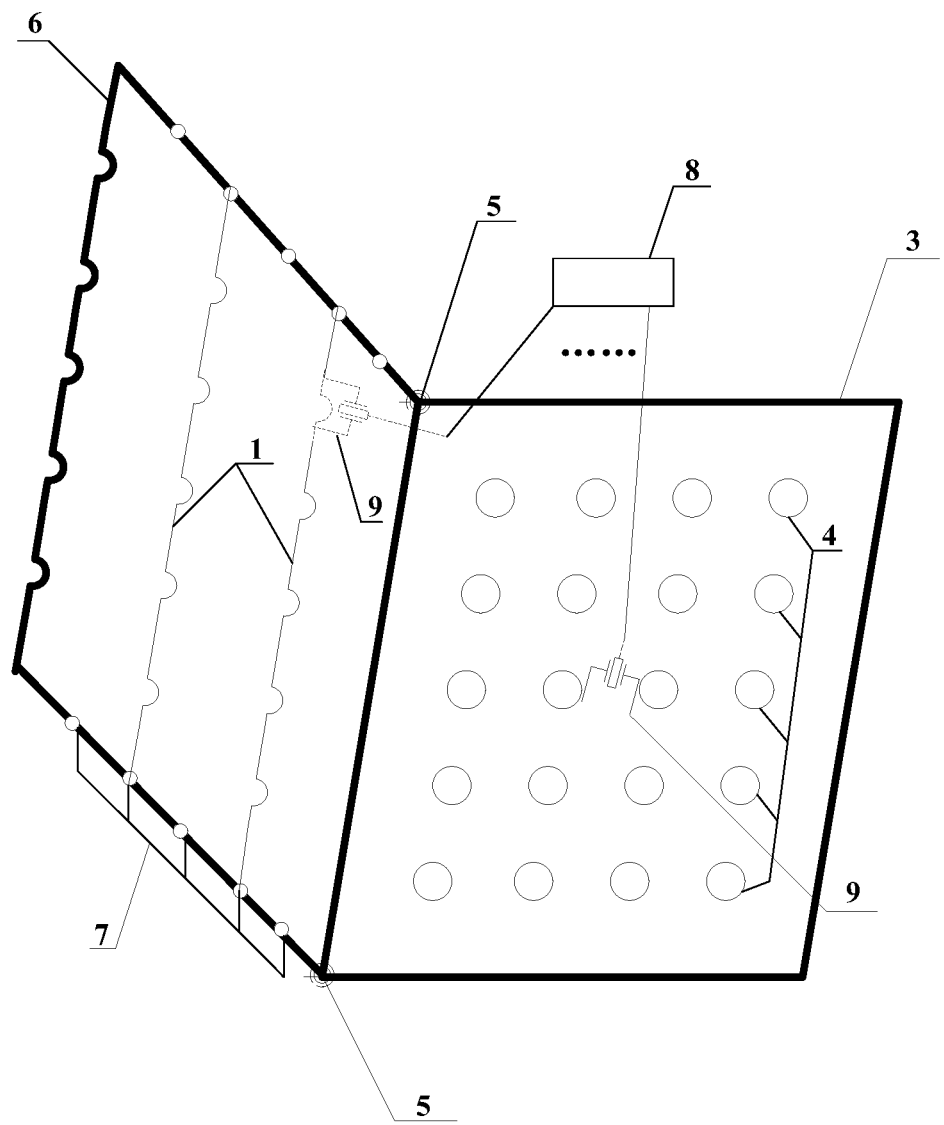
FIG. 1 is a structurally schematic drawing depicting a multi-function cooling and thermo-sensitive rack for microbiology experiment according to Embodiment 1 of the present invention.

Referring to FIG. 1, in the present embodiment, a multi-function cooling and thermo-sensitive rack for microbiology experiment comprises horizontal bars 1 having a plurality of semicircular positioning dents, a base 3, connectors 5, a lateral frame 6, connecting holes 7, a temperature-displaying prompter 8, and N temperature sensors 9, where N is an integer greater than or equal to one. The lateral frame 6 is a U-shaped frame. The base 3 has positioning holes 4. The lateral frame 6 and the base 3 are dimensionally identical to each other. The lateral frame 6 and the base 3 are connected through the connectors 5. The arms of the U-shaped frame of the lateral frame 6 are provided symmetrically with plural said connecting holes 7. The horizontal bars 1 are horizontally mounted on the connecting holes 7. The N temperature sensors 9 are located at N temperature-measured sites, respectively. The N temperature sensors 9 have output ends for outputting temperature-sensing signals connected with input ends of the temperature-displaying prompters 8 for inputting the N temperature-sensing signals.

Embodiment 2

Figure 2:
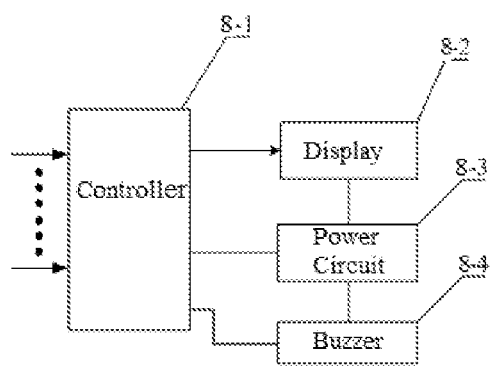
FIG. 2 is a structurally schematic drawing depicting a temperature-displaying prompter according to Embodiment 2 of the present invention.

Referring to FIG. 2, the present embodiment further delimits the multi-function cooling and thermo-sensitive rack for microbiology experiment disclosed in Embodiment 1. The temperature-displaying prompter 8 comprises a controller 8-1, a display 8-2, a power circuit 8-3, and a buzzer 8-4. The power output ends of the power circuit 8-3 connect with the power input end of the controller 8-1, the power input end of the display 8-2, and the power input end of the buzzer 8-4, respectively. The input ends of the controller 8-1 for inputting the N temperature-sensing signals connect with the output ends of the N temperature sensors 9 for outputting the sensing signals. The output end of the controller 8-1 for outputting the displaying signal connects with the input end of the display 8-2 for inputting the displaying signal. The output of the controller 8-1 for outputting the buzzer-activating control signal connects with the input end of the buzzer 8-4 for inputting the buzzer-activating control signal.

The present embodiment may be set that when any of the temperature sensors detects a temperature that is suitable for inoculation and pouring solid medium, the buzzer (8-4) buzzes.

Embodiment 3

Referring to FIGS. 1 and 2, the present embodiment further delimits the multi-function cooling and thermo-sensitive rack for microbiology experiment disclosed in Embodiment 2. The controller 8-1 is a single-chip microcontroller.

Embodiment 4

Referring to FIG. 1, the present embodiment further delimits the multi-function cooling and thermo-sensitive rack for microbiology experiment disclosed in Embodiment 1. The positioning dents are evenly distributed over the horizontal bar 1.

Embodiment 5

Referring to FIG. 1, the present embodiment further delimits the multi-function cooling and thermo-sensitive rack for microbiology experiment disclosed in Embodiment 1. The lateral frame 6 is formed by heat resistant frame.

Embodiment 6

Referring to FIG. 1, the present embodiment further delimits the multi-function cooling and thermo-sensitive rack for microbiology experiment disclosed in Embodiment 1. The base 3 is formed by heat resistant base.

Embodiment 7

Figure 3:
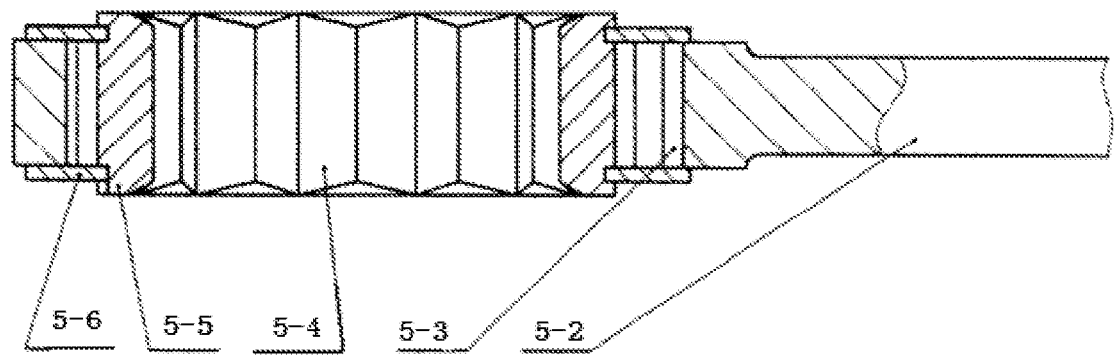
FIG. 3 is a cross-sectional view of a reversible ratchet mechanism of a connector 5 according to Embodiment 7 of the present invention.
Figure 4:
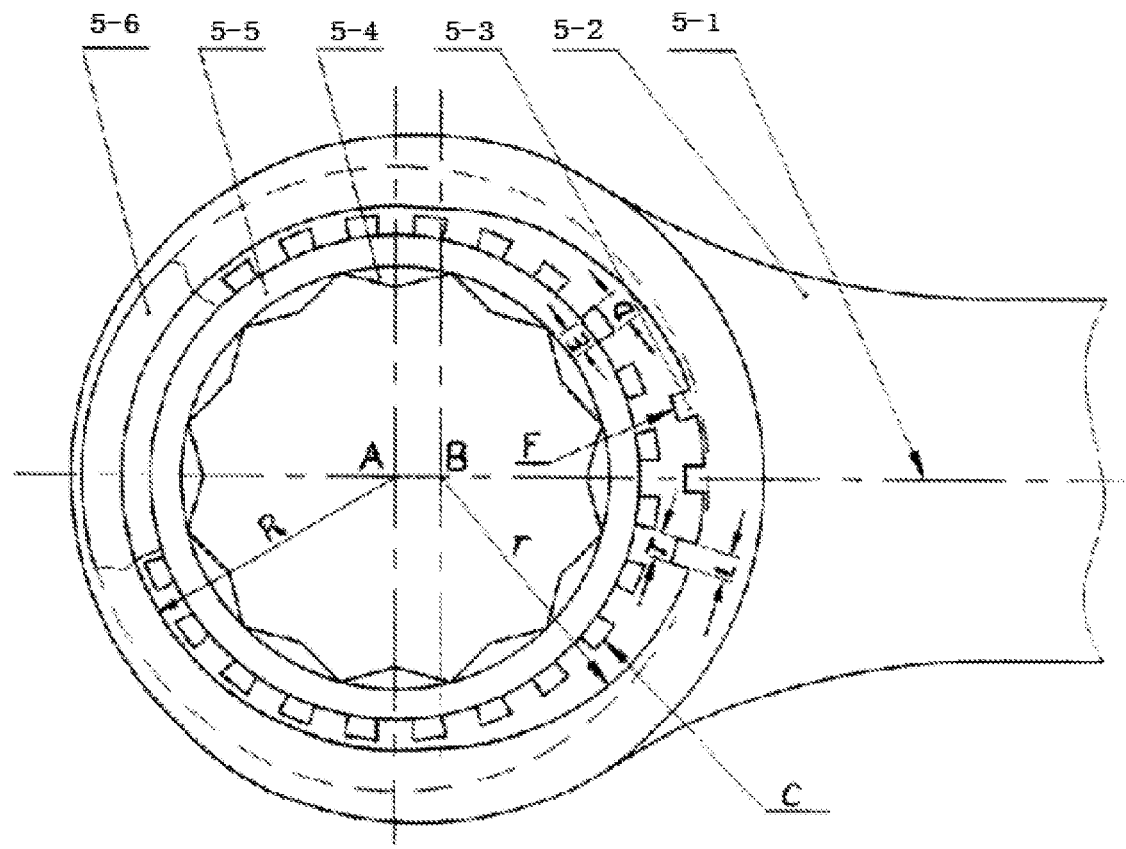
FIG. 4 is a plan view of the reversible ratchet mechanism of a connector 5 according to Embodiment 7 of the present invention.

Referring to FIGS. 1, 3, and 4, the present embodiment further delimits the multi-function cooling and thermo-sensitive rack for microbiology experiment disclosed in Embodiment 1. The connector 5 comprises a reversible ratchet mechanism.

The connectors 5 each has a through hole that has two coplanar circle centers A, B. Up to twenty internal teeth 5-3 are formed on the wall of the through hole symmetrically against a point that is an intersection point of an imaginary connecting line linking the circle centers (A, B) and one site R or r on the wall of the through hole. A ratchet 5-5 that has an outer wall peripherally formed with a row of teeth is received in the through hole. The ratchet 5-5 is configured to radially move to and fro toward either of the circle centers A and B. The teeth of the ratchet 5-5 can engage with each of the internal teeth 5-3, so as to radially rotate in either direction as a whole or to rotate independently of each other. A handle 5-2 extends radially outward from outer periphery of the through hole. The middle line of handle 5-2 is a center line 5-1. The center line 5-1 coincides with, is parallel to, or intersects the imaginary connecting line linking the circle centers A and B. The ratchet 5-5 is provided with a nut-fitting hole, a square insert, or a mechanical workpiece 5-4. Each of the teeth of the ratchet 5-5 has a curved top surface C and has a top width D equal to or greater than a root width E. Each of the internal teeth 5-3 has a curved or flat top surface F and has a top width T equal to or greater than a root width L. The outer periphery of opposite ends of the ratchet 5-5 has two retaining rings 5-6 for retaining the ratchet 5-5 in the through hole and two recesses for receiving two retaining rings 5-6. The retaining rings 5-6 are spring loops cut at a radius thereof.

In use, by radially pushing the handle 5-2 slightly and bringing the internal teeth 5-3 near the handle 5-2 engaged with the teeth of the ratchet 5-5, the rack can be radially rotated and thus expanded. On the other hand, by radially pulling the handle 5-2 slightly, the internal teeth 5-3 are disengaged from the teeth of the ratchet 5-5, so that the handle 5-2 is allowed to be rotated reversely to collapse the rack.

The present invention features for the positioning circular holes formed on the base, and also features for the connection based on the reversible ratchet mechanism between the base and the lateral frame, and the angular adjustability thereof, so that different needs of experiments can be met. The connector uses a reversible ratchet mechanism to control the open angle formed by the base and the lateral frame, while the lateral frame can be well positioned and supported. The horizontal bars having the positioning dents are heat resistant and directly mounted on the lateral frame. These horizontal bars can be selectively arranged at different sites on the lateral frame for meeting various needs. In use, an inoculation loop or applicator may have its lower end inserted in a positioning hole, and have its upper end leant against a positioning dent. Erlenmeyer flasks can be placed on the base. The sensors may be arranged at different sites on the rack for sensing the temperatures of heated culture medium in Erlenmeyer flasks or flamed experimental tools such as inoculation loops and applicators. When a heated Erlenmeyer flask containing the sterilized culture medium is placed on the temperature sensor, the temperature-displaying prompter can display the temperature of the culture medium, and the buzzer buzzes when this temperature reaches a setting value required by the ongoing experiment, thereby helping to prevent the culture medium from being overheated or overcooled which will affect results of the experiment. The temperatures of flamed inoculation loops and/or applicators sensed by the temperature sensors can be read out at the display of the prompter, thereby enabling immediate determination about whether it's time to perform inoculation, so as to improve test accuracy and efficiency.

The advancement of the present invention includes: (1) reasonable design because the disclosed rack is structurally simple and angularly adjustable and can be assembled according to its use; (2) extensive use because the disclosed rack can well support various tools such as inoculation loops and/or applicators that are sterilized by open flame, and the disclosed rack can sense temperatures of experiment devices such as inoculation loops, applicators and Erlenmeyer flasks; and (3) value-added functions provided by the temperature sensors and the temperature-displaying prompter, which help to reduce faults in experiments, thereby improving test efficiency.

Embodiment 8

Referring to FIG. 1, the present embodiment further delimits the multi-function cooling and thermo-sensitive rack for microbiology experiment disclosed in Embodiment 1. The base 3 contains therein a temperature-lowering substance.

It is possible to change the material and thickness of the base 3 according to the properties of the temperature-lowering substance and actual requirements for cooling.

Embodiment 9

Referring to FIG. 1, the present embodiment further delimits the multi-function cooling and thermo-sensitive rack for microbiology experiment disclosed in Embodiment 8. The temperature-lowering substance can be removed from the base 3.

The present embodiment may use a reusable temperature-lowering substance.

Embodiment 10

Referring to FIG. 1, the present embodiment further delimits the multi-function cooling and thermo-sensitive rack for microbiology experiment disclosed in Embodiment 8 or 9. The temperature-lowering substance is a cooling pack.

Embodiment 11

Referring to FIG. 1, the present embodiment further delimits the multi-function cooling and thermo-sensitive rack for microbiology experiment disclosed in Embodiment 10. The cooling pack is a chemical cooling pack or a physical cooling pack.

The chemical cooling pack may be a chemical ice pack that is made of sodium sulfate decahydrate, ammonium hydrogen sulfate, sodium hydrogen sulfate, and ammonium nitrate.

Embodiment 12

Referring to FIG. 1, the present embodiment further delimits the multi-function cooling and thermo-sensitive rack for microbiology experiment disclosed in Embodiment 11. The physical cooling pack is a dry ice pack, a water ice pack, a water-salt ice pack, or a water-ethanol ice pack.

The physical cooling pack is reusable. The multi-function cooling and thermo-sensitive rack for microbiology experiment can be placed into a refrigerating appliance (e.g. a refrigerator or an icebox) as a whole. Alternatively, the physical cooling pack can be removed from the rack and placed into a refrigerating appliance alone.

Embodiment 13

Figure 5:
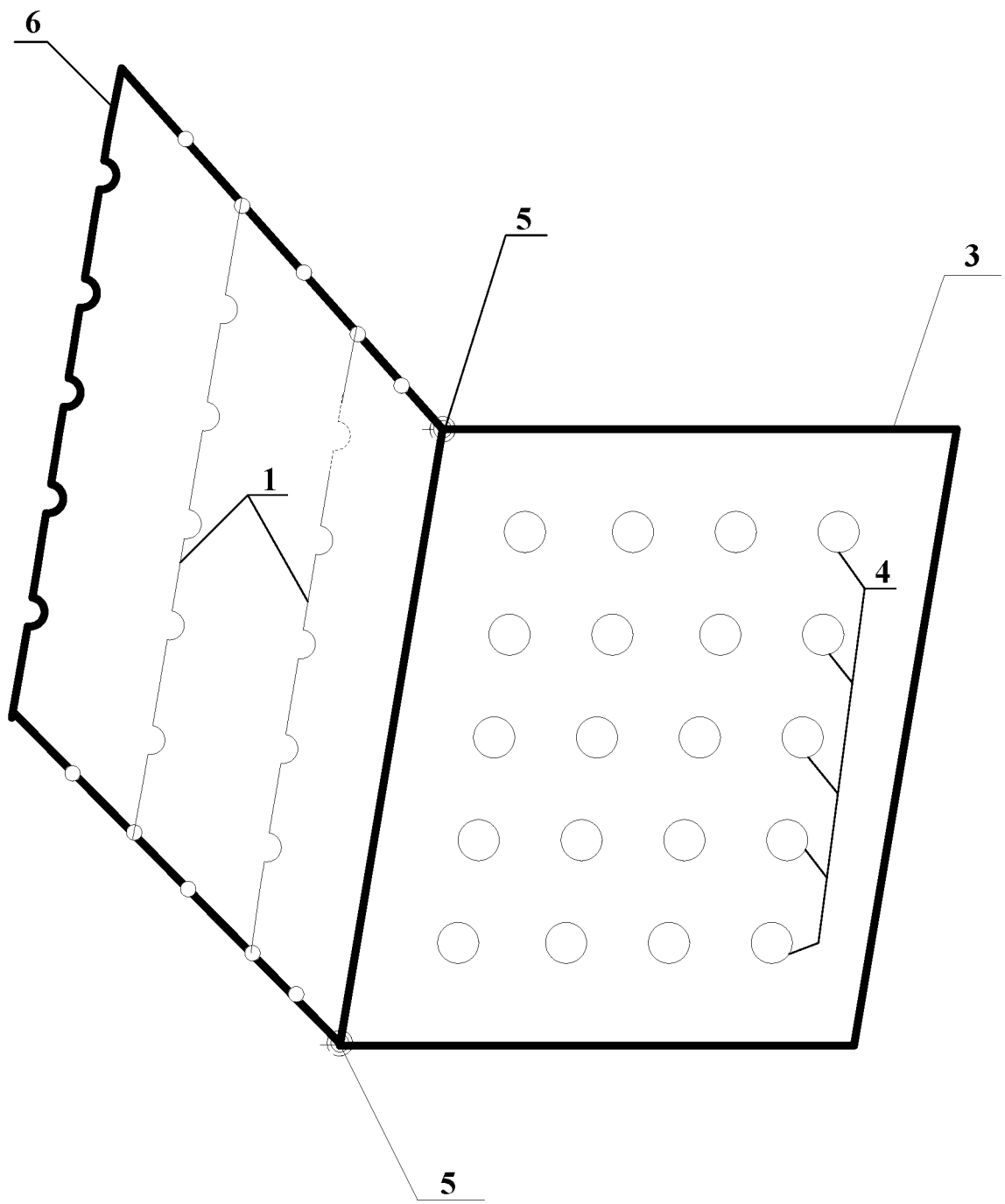
FIG. 5 is a structurally schematic drawing depicting a multi-function cooling and thermo-sensitive rack for microbiology experiment according to Embodiment 13 of the present invention.

Referring to FIG. 5, in the present embodiment, a multi-function cooling and thermo-sensitive rack for microbiology experiment comprises horizontal bars 1 having a plurality of semicircular positioning dents, a base 3, connectors 5, and a lateral frame 6. The lateral frame 6 is a U-shaped frame. The base 3 has positioning holes 4. The lateral frame 6 and the base 3 are dimensionally identical to each other, the lateral frame 6 and the base 3 are connected through the connectors 5. The horizontal bars 1 are horizontally mounted on the arms of the U-shaped frame of the lateral frame 6. The horizontal bars 1 and/or the base 3 are thermochromic.

Embodiment 14

Referring to FIG. 5, the present embodiment further delimits the multi-function cooling and thermo-sensitive rack for microbiology experiment disclosed in Embodiment 13. The positioning dents are evenly distributed over the horizontal bar 1.

Embodiment 15

Referring to FIG. 5, the present embodiment further delimits the multi-function cooling and thermo-sensitive rack for microbiology experiment disclosed in Embodiment 13. The lateral frame 6 is formed by heat resistant frame.

Embodiment 16

Referring to FIG. 5, the present embodiment further delimits the multi-function cooling and thermo-sensitive rack for microbiology experiment disclosed in Embodiment 13. The base 3 is formed by heat resistant base.

Embodiment 17

Referring to FIGS. 3, 4, and 5, the present embodiment further delimits the multi-function cooling and thermo-sensitive rack for microbiology experiment disclosed in Embodiment 13. The connector 5 comprises a reversible ratchet mechanism.

Embodiment 18

Referring to FIG. 5, the present embodiment further delimits the multi-function cooling and thermo-sensitive rack for microbiology experiment disclosed in Embodiment 13. The base 3 contains therein a temperature-lowering substance.

It is possible to change the material and thickness of the base 3 according to the properties of the temperature-lowering substance and actual requirements for cooling.

Embodiment 19

Referring to FIG. 5, the present embodiment further delimits the multi-function cooling and thermo-sensitive rack for microbiology experiment disclosed in Embodiment 18. The temperature-lowering substance can be removed from the base 3.

Embodiment 20

Referring to FIG. 5, the present embodiment further delimits the multi-function cooling and thermo-sensitive rack for microbiology experiment disclosed in Embodiment 18 or 19. The temperature-lowering substance is an ice pack.

Embodiment 21

Referring to FIG. 5, the present embodiment further delimits the multi-function cooling and thermo-sensitive rack for microbiology experiment disclosed in Embodiment 20. The ice pack is a chemical ice pack or a physical ice pack.

Embodiment 22

Referring to FIG. 5, the present embodiment further delimits the multi-function cooling and thermo-sensitive rack for microbiology experiment disclosed in Embodiment 21. The physical ice pack is a dry ice pack, a water ice pack, a water-salt ice pack, or a water-ethanol ice pack.

The physical ice pack is reusable. The multi-function cooling and thermo-sensitive rack for microbiology experiment disclosed can be placed into a refrigerating appliance (e.g. a refrigerator or an icebox) as a whole. Alternatively, the physical ice pack can be removed from the rack and placed into a refrigerating appliance alone.

Embodiment 23

Referring to FIG. 5, the present embodiment further delimits the multi-function cooling and thermo-sensitive rack for microbiology experiment disclosed in Embodiment 13. The horizontal bars 1 and/or the base 3 include a thermochromic material.

Embodiment 24

Referring to FIG. 5, the present embodiment further delimits the multi-function cooling and thermo-sensitive rack for microbiology experiment disclosed in Embodiment 23. The thermochromic material is thermochromic microencapsulated powder, thermochromic powder, thermochromic emulsion, thermochromic color master batch, or thermochromic ink.

The thermochromic material may be set that it changes its color when it is higher than a temperature that is suitable for inoculation and pouring solid medium, or that it changes its color when it is lower than the temperature that is suitable for inoculation and pouring solid medium.

The thermochromic microencapsulated powder, thermochromic powder, thermochromic emulsion, thermochromic color master batch, or thermochromic ink is commercially available at chemistry companies.

The thermochromic microencapsulated powder, thermochromic powder, thermochromic emulsion, thermochromic color master batch or thermochromic ink is commercially available at Bianse Chemistry Co., Ltd., Shenzhen City, China.

Embodiment 25

Figure 6:
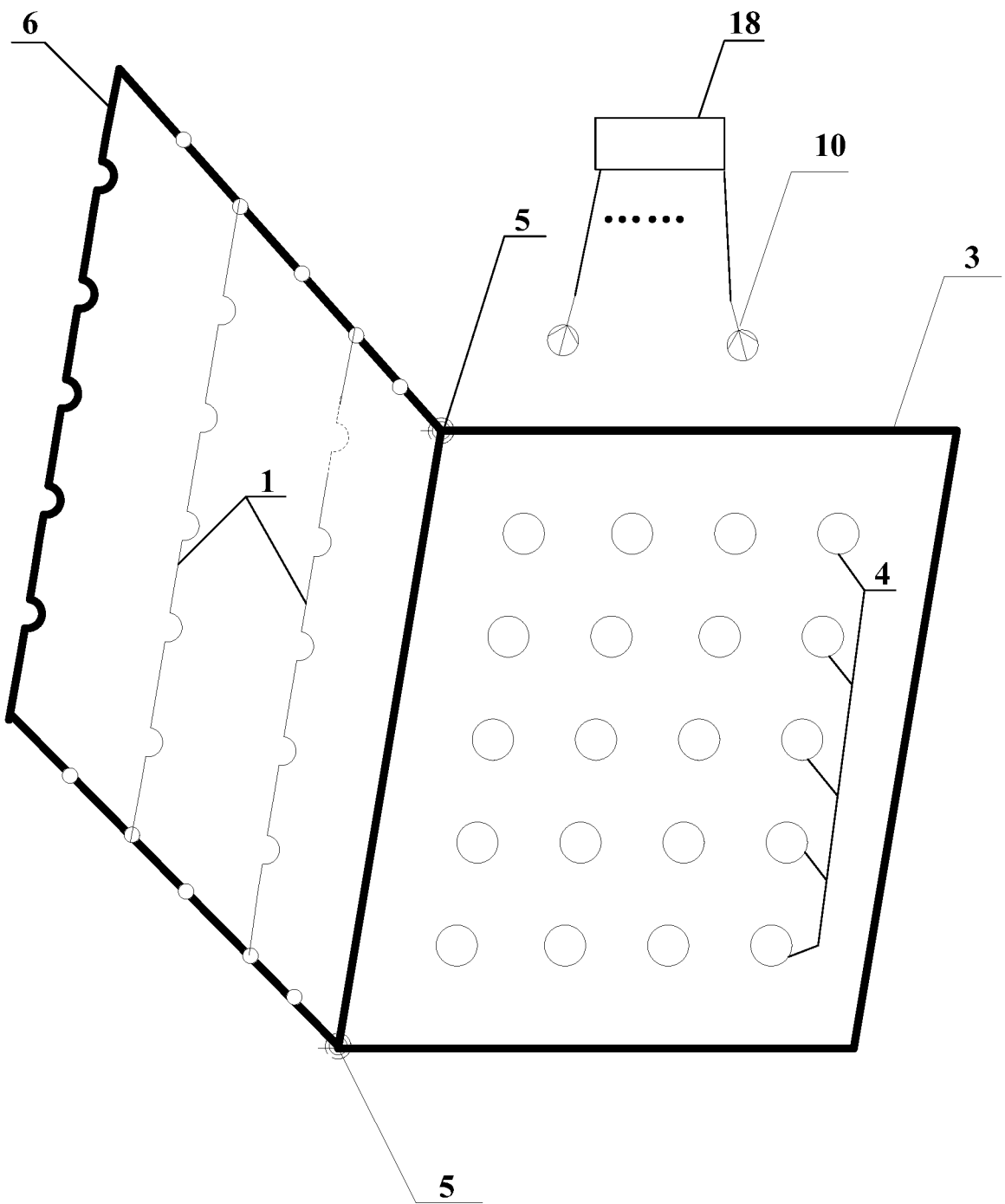
FIG. 6 is a structurally schematic drawing depicting a multi-function cooling and thermo-sensitive rack for microbiology experiment according to Embodiment 25 of the present invention.

Referring to FIG. 6, in the present embodiment, a multi-function cooling and thermo-sensitive rack for microbiology experiment comprises horizontal bars 1 having a plurality of semicircular positioning dents, a base 3, connectors 5, a lateral frame 6, a temperature prompter 18, and infrared temperature sensors 10. The lateral frame 6 is a U-shaped frame. The base 3 has positioning holes 4. The lateral frame 6 and the base 3 are dimensionally identical to each other.

The lateral frame 6 and the base 3 are connected through the connectors 5. The horizontal bars 1 are horizontally mounted on the arms of the U-shaped frame of the lateral frame 6. The infrared temperature sensor 10 has an output end for outputting a sensing signal connected with an input end of the temperature prompter 18 for inputting the temperature-sensing signal.

There are N infrared temperature sensors 10, where N is an integer greater than or equal to one. Each of the infrared temperature sensors 10 is dedicated to measure one experimental tool placed on the multi-function cooling and thermo-sensitive rack.

Embodiment 26

Figure 7:
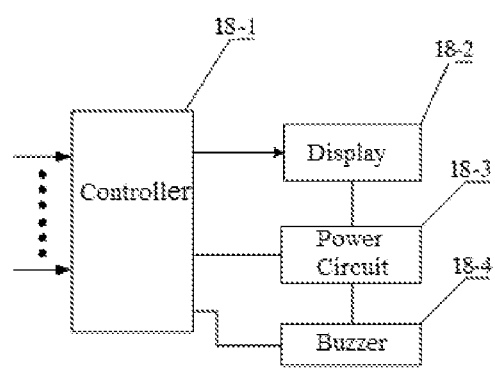
FIG. 7 is a structurally schematic drawing depicting a temperature prompter according to Embodiment 26 of the present invention.

Referring to FIGS. 7 and 6, the present embodiment further delimits the multi-function cooling and thermo-sensitive rack for microbiology experiment disclosed in Embodiment 25. The temperature prompter 18 comprises a controller 18-1 and a power circuit 18-3, and further comprises a display 18-2 and/or a buzzer 18-4. The power circuit 18-3 has its power output end connected with the power input end of the controller 18-1, the power input end of the display 18-2, and the power input end of the buzzer 18-4, respectively. An input end of the controller 18-1 for inputting each of the temperature-sensing signals is connected with an output end of one infrared temperature sensor 10 for outputting the sensing signal. The output end of the controller 18-1 for outputting the displaying signal is connected with the input end of the display 18-2 for inputting the displaying signal. The output end of the controller 18-1 for outputting the buzzer-activating control signal is connected with the input end of the buzzer 18-4 for inputting the buzzer-activating control signal.

It may be set that when any of the infrared temperature sensors 10 detects a temperature that is lower than the temperature suitable for inoculation and pouring solid medium, the buzzer 18-4 buzzes.

Embodiment 27

Referring to FIGS. 7 and 6, the present embodiment further delimits the multi-function cooling and thermo-sensitive rack for microbiology experiment disclosed in Embodiment 25. The controller 18-1 is a single-chip microcontroller.

Embodiment 28

Referring to FIG. 6, the present embodiment further delimits the multi-function cooling and thermo-sensitive rack for microbiology experiment disclosed in Embodiment 25. The positioning dents are evenly distributed over the horizontal bar 1.

Embodiment 29

Referring to FIG. 6, the present embodiment further delimits the multi-function cooling and thermo-sensitive rack for microbiology experiment disclosed in Embodiment 25. The lateral frame 6 is formed by heat resistant frame.

Embodiment 30

Referring to FIG. 6, the present embodiment further delimits the multi-function cooling and thermo-sensitive rack for microbiology experiment disclosed in Embodiment 25. The base 3 is formed by heat resistant base.

Embodiment 31

Referring to FIGS. 3, 4, and 6, the present embodiment further delimits the multi-function cooling and thermo-sensitive rack for microbiology experiment disclosed in Embodiment 25. The connector 5 comprises a reversible ratchet mechanism.

Embodiment 32

Referring to FIG. 6, the present embodiment further delimits the multi-function cooling and thermo-sensitive rack for microbiology experiment disclosed in Embodiment 25. The base 3 contains therein a temperature-lowering substance.

It is possible to change the material and thickness of the base 3 according to the properties of the temperature-lowering substance and actual requirements for cooling.

Embodiment 33

Referring to FIG. 6, the present embodiment further delimits the multi-function cooling and thermo-sensitive rack for microbiology experiment disclosed in Embodiment 32. The temperature-lowering substance can be removed from the base 3.

Embodiment 34

Referring to FIG. 6, the present embodiment further delimits the multi-function cooling and thermo-sensitive rack for microbiology experiment disclosed in Embodiment 32 or 33. The temperature-lowering substance is a cooling pack.

Embodiment 35

Referring to FIG. 6, the present embodiment further delimits the multi-function cooling and thermo-sensitive rack for microbiology experiment disclosed in Embodiment 34. The cooling pack is a chemical cooling pack or a physical cooling pack.

Embodiment 36

Referring to FIG. 6, the present embodiment further delimits the multi-function cooling and thermo-sensitive rack for microbiology experiment disclosed in Embodiment 35. The physical cooling pack is a dry ice pack, a water ice pack, a water-salt ice pack, or a water-ethanol ice pack.

The physical cooling pack is reusable. The multi-function cooling and thermo-sensitive rack for microbiology experiment can be placed into a refrigerating appliance (e.g. a refrigerator or an icebox) as a whole. Alternatively, the physical cooling pack can be removed from the rack and placed into a refrigerating appliance alone.

Embodiment 37

Figure 8:
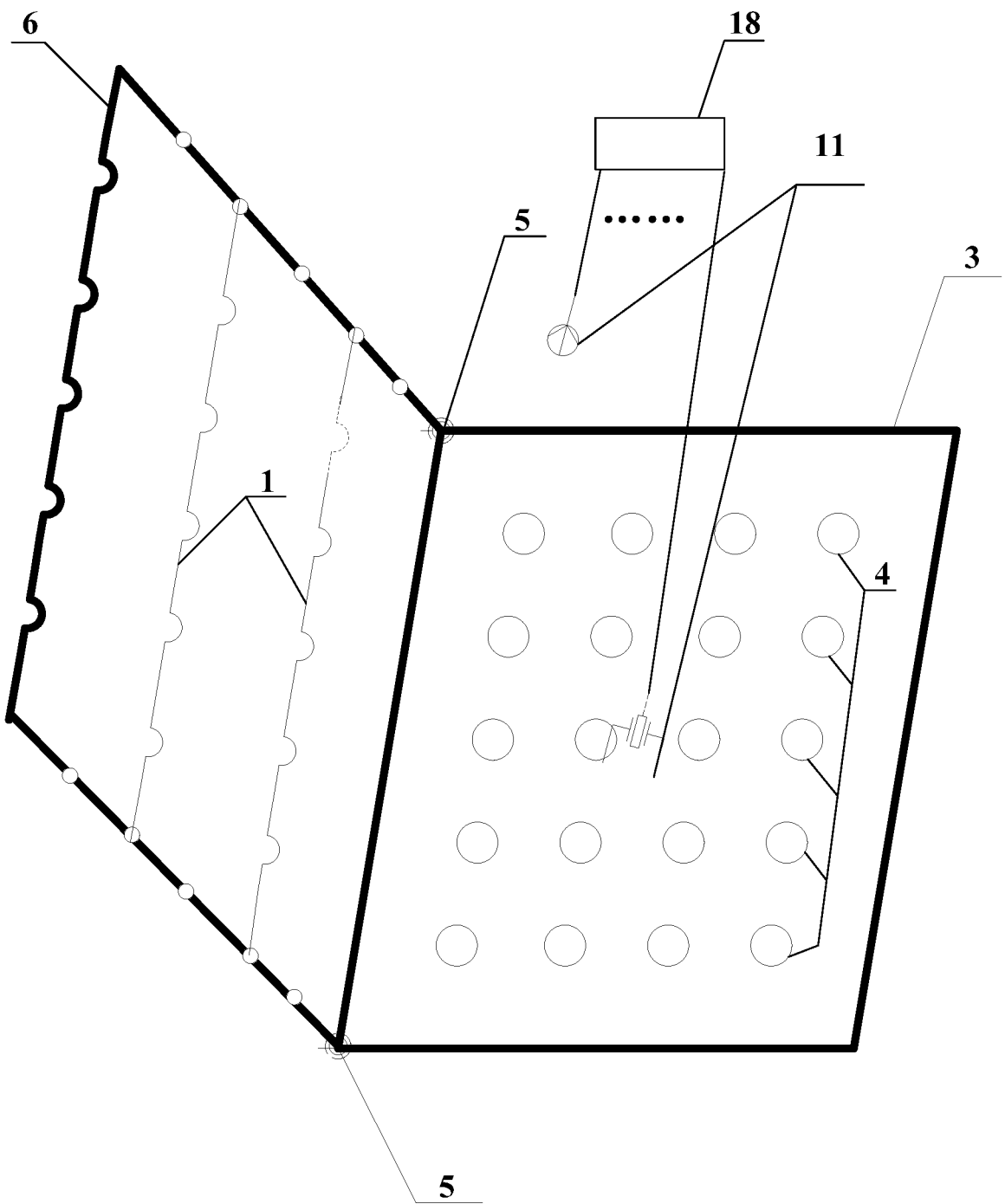
FIG. 8 is a structurally schematic drawing depicting a multi-function cooling and thermo-sensitive rack for microbiology experiment according to Embodiment 37 of the present invention.

Referring to FIG. 7 and FIG. 8, in the present embodiment, a multi-function cooling and thermo-sensitive rack for microbiology experiment comprises horizontal bars 1 having a plurality of semicircular positioning dents, a base 3, connectors 5, a lateral frame 6, temperature sensors 11 and a temperature prompter 18. The lateral frame 6 is a U-shaped frame. The base 3 has positioning holes 4. The lateral frame 6 and the base 3 are dimensionally identical to each other. The lateral frame 6 and the base 3 are connected through the connectors 5. The horizontal bars 1 are horizontally mounted on the arms of the U-shaped frame of the lateral frame 6. The temperature sensor 11 has an output end for outputting a sensing signal connected with an input end of the temperature prompter 18 for inputting the temperature-sensing signal. The temperature prompter 18 comprises a controller 18-1 and a power circuit 18-3, and further comprises a display 18-2 and/or a buzzer 18-4. The power circuit 18-3 has its power output end connected with the power input end of the controller 18-1, the power input end of the display 18-2, and the power input end of the buzzer 18-4, respectively. An input end of the controller 18-1 for inputting each of the temperature-sensing signals is connected with an output end of one temperature sensor 11 for outputting the sensing signal. The output end of the controller 18-1 for outputting the displaying signal is connected with the input end of the display 18-2 for inputting the displaying signal. The output end of the controller 18-1 for outputting the buzzer-activating control signal is connected with the input end of the buzzer 18-4 for inputting the buzzer-activating control signal.

It may be set that when any of the temperature sensors 11 detects a temperature that is lower than the temperature suitable for inoculation and pouring solid medium, the buzzer 18-4 buzzes. There are N temperature sensors 11, where N is an integer greater than or equal to one. Each of the temperature sensors 11 is dedicated to measure one experimental tool placed on the multi-function cooling and thermo-sensitive rack.

Embodiment 38

Referring to FIG. 1, the present embodiment further delimits the multi-function cooling and thermo-sensitive rack for microbiology experiment disclosed in Embodiment 11. The chemical cooling pack is a chemical ice pack.

Embodiment 39

Referring to FIG. 1, the present embodiment further delimits the multi-function cooling and thermo-sensitive rack for microbiology experiment disclosed in Embodiment 38. The chemical ice pack is made of sodium sulfate decahydrate, ammonium hydrogen sulfate, sodium hydrogen sulfate, and ammonium nitrate.

Embodiment 40

Referring to FIG. 1, the present embodiment further delimits the multi-function cooling and thermo-sensitive rack for microbiology experiment disclosed in Embodiment 12. The water-salt ice pack is made of $CaCl_2$ and water, or of $NH_4Cl$ and water, or of $NH_4NO_3$, $Na_2CO_3$ and water.

Embodiment 41

Referring to FIG. 5, the present embodiment further delimits the multi-function cooling and thermo-sensitive rack for microbiology experiment disclosed in Embodiment 21. The chemical cooling pack is a chemical ice pack.

Embodiment 42

Referring to FIG. 5, the present embodiment further delimits the multi-function cooling and thermo-sensitive rack for microbiology experiment disclosed in Embodiment 41. The chemical ice pack is made of sodium sulfate decahydrate, ammonium hydrogen sulfate, sodium hydrogen sulfate, and ammonium nitrate.

Embodiment 43

Referring to FIG. 5, the present embodiment further delimits the multi-function cooling and thermo-sensitive rack for microbiology experiment disclosed in Embodiment 22. The water-salt ice pack is made of $CaCl_2$ and water, or of $NH_4Cl$ and water, or of $NH_4NO_3$, $Na_2CO_3$ and water.

Embodiment 44

Referring to FIG. 6, the present embodiment further delimits the multi-function cooling and thermo-sensitive rack for microbiology experiment disclosed in Embodiment 35. The chemical cooling pack is a chemical ice pack.

Embodiment 45

Referring to FIG. 6, the present embodiment further delimits the multi-function cooling and thermo-sensitive rack for microbiology experiment disclosed in Embodiment 44. The chemical ice pack is made of sodium sulfate decahydrate, ammonium hydrogen sulfate, sodium hydrogen sulfate, and ammonium nitrate.

Embodiment 46

Referring to FIG. 6, the present embodiment further delimits the multi-function cooling and thermo-sensitive rack for microbiology experiment disclosed in Embodiment 36. The water-salt ice pack is made of $CaCl_2$ and water, or of $NH_4Cl$ and water, or of $NH_4NO_3$, $Na_2CO_3$ and water.

Embodiment 47

Referring to FIGS. 7 and 8, the present embodiment further delimits the multi-function cooling and thermo-sensitive rack for microbiology experiment disclosed in Embodiment 37. The controller 18-1 is a single-chip microcontroller.

Embodiment 48

Referring to FIGS. 3, 4, and 8, the present embodiment further delimits the multi-function cooling and thermo-sensitive rack for microbiology experiment disclosed in Embodiment 37. The connector 5 comprises a reversible ratchet mechanism.

Embodiment 49

Referring to FIG. 8, the present embodiment further delimits the multi-function cooling and thermo-sensitive rack for microbiology experiment disclosed in Embodiment 37. The base 3 contains therein a temperature-lowering substance.

What is claimed is:
1. A multi-function cooling and thermo-sensitive rack for microbiology experiments, characterized in that,
the multi-function cooling and thermo-sensitive rack comprising a lateral frame and a base connected by angle adjustable connectors, wherein the lateral frame and the base are provided respectively with at least one horizontal bar having a plurality of positioning dents and at least one positioning hole, which are used to place and fix experiment devices in the positioning dents and the positioning holes,
wherein temperatures of the experiment devices are sensed and displayed by at least one temperature sensor arranged at least one temperature-measured site of the lateral frame and the base and at least one temperature-displaying prompter connected with the at least one temperature sensor; or by the horizontal bar and base,
at least one of the connectors comprises a reversible ratchet mechanism,
wherein at least one of the connectors has a through hole that has two coplanar circle centers A, B, internal teeth are formed symmetrically on the wall of the through hole, wherein the ratchet that has an outer wall peripherally formed with a row of teeth is received in the through hole, the ratchet can radially move to and fro toward either of the circle centers A and B, and wherein the teeth of the ratchet can engage with each of the internal teeth,
wherein a handle extends radially outward from outer periphery of the through hole, a center axis of the handle is a center line of the handle, the center line of the handle coincides with, is parallel to, or intersects the imaginary connecting line linking the circle centers A and B, and wherein the ratchet is provided with a nut-fitting hole, a square insert, or a mechanical workpiece,
wherein each of the teeth of the ratchet has a curved top surface C and has a top width D equal to or greater than a root width E, each of the internal teeth has a curved or flat top surface F and has a top width T equal to or greater than a root width L, wherein two retaining rings that retain the ratchet in the through hole and two recesses for receiving the retaining rings are formed at the outer periphery of opposite ends of the ratchet, and wherein the retaining rings are a spring loop cut at a radius thereof.
2. The multi-function cooling and thermo-sensitive rack for microbiology experiments of claim 1, wherein the positioning dents and the positioning hole are temperature-measured sites, and wherein the at least one temperature sensor is arranged at the positioning dents or the positioning holes.
3. The multi-function cooling and thermo-sensitive rack for microbiology experiments of claim 2, wherein the temperature-displaying prompter comprises:
a controller receiving temperature-sensing signals from the temperature sensors and transmitting temperature displaying signals and buzzer-activating control signals,
a display receiving temperature displaying signals from the controller,
a buzzer receiving buzzer-activating control signals from the controller and buzzing according to the buzzer-activating control signals,
and a power circuit powering the controller, the display and the buzzer.
4. The multi-function cooling and thermo-sensitive rack for microbiology experiments of claim 3, wherein the power circuit has a power output end connected with a power input end of the controller, a power input end of the display, and a power input end of the buzzer, respectively;
wherein an input end of the controller for inputting at least one temperature-sensing signal is connected with an output end of the at least one temperature sensor for outputting the sensing signal;
wherein an output end of the controller for outputting a displaying signal is connected with an input end of the display for inputting the displaying signal;
and wherein an output end of the controller for outputting a buzzer-activating control signal is connected with an input end of the buzzer for inputting the buzzer-activating control signal.

5. The multi-function cooling and thermo-sensitive rack for microbiology experiments of claim 3, wherein controller is a single-chip microcontroller.

6. The multi-function cooling and thermo-sensitive rack for microbiology experiments of claim 1, wherein the horizontal bars and the base include thermochromic material, and wherein the thermochromic material is thermochromic microencapsulated powder, thermochromic powder, thermochromic emulsion, thermochromic color master batch, or thermochromic ink.

7. The multi-function cooling and thermo-sensitive rack for microbiology experiments of claim 1, wherein the at least one temperature sensor is an infrared temperature sensor.

8. The multi-function cooling and thermo-sensitive rack for microbiology experiments of claim 1, wherein arms of the lateral frame are provided symmetrically with plural connecting holes for horizontally fixing the horizontal bars.

9. The multi-function cooling and thermo-sensitive rack for microbiology experiments of claim 1, wherein the lateral frame and the base are U-shaped frames of the same dimension.

10. The multi-function cooling and thermo-sensitive rack for microbiology experiments of claim 9, wherein the lateral frame and the base are U-shaped frames of the same length.

11. The multi-function cooling and thermo-sensitive rack for microbiology experiments of claim 1, wherein the positioning dents are semicircular positioning dents and evenly distributed over the horizontal bars.

12. The multi-function cooling and thermo-sensitive rack for microbiology experiments of claim 1, wherein the horizontal bars are heat resistant horizontal bars, the lateral frame is formed by heat resistant frame, the base contains therein a removable temperature-lowering substance, the temperature-lowering substance is a chemical cooling pack or a physical cooling pack,
wherein the chemical cooling pack is a chemical ice pack that is made of sodium sulfate decahydrate, ammonium hydrogen sulfate, sodium hydrogen sulfate, and ammonium nitrate;
wherein the physical cooling pack is a dry ice pack, a water ice pack, a water-salt ice pack, or a water-ethanol ice pack.

* * * * *